United States Patent
Wang et al.

(10) Patent No.: US 8,829,167 B2
(45) Date of Patent: Sep. 9, 2014

(54) FOLIAMANGIFEROSIDES, PREPARATION METHOD AND USE THEREOF

(75) Inventors: Tao Wang, Tianjin (CN); Yi Zhang, Tianjin (CN); Erwei Liu, Tianjin (CN); Lifeng Han, Tianjin (CN); Dandan Ge, Tianjin (CN); Xiumei Gao, Tianjin (CN)

(73) Assignee: Tianjin University of Traditional Chinese Medicine, Tianjin (CN)

( * ) Notice: Subject to any disclaimer, the term of this patent is extended or adjusted under 35 U.S.C. 154(b) by 73 days.

(21) Appl. No.: 13/501,208

(22) PCT Filed: Sep. 30, 2010

(86) PCT No.: PCT/CN2010/001544
§ 371 (c)(1),
(2), (4) Date: Apr. 10, 2012

(87) PCT Pub. No.: WO2011/044751
PCT Pub. Date: Apr. 21, 2011

(65) Prior Publication Data
US 2012/0202755 A1    Aug. 9, 2012

(30) Foreign Application Priority Data
Oct. 16, 2009    (CN) .......................... 2009 1 0070845

(51) Int. Cl.
*C07H 1/00*       (2006.01)
*A01N 43/04*    (2006.01)
*A61K 31/70*    (2006.01)

(52) U.S. Cl.
USPC ............................................ 536/1.11; 514/23

(58) Field of Classification Search
None
See application file for complete search history.

(56) References Cited

FOREIGN PATENT DOCUMENTS

| CN | 1488355 A | 4/2004 |
|---|---|---|
| CN | 1733785 A | 2/2006 |
| CN | 100998601 A | 7/2007 |
| CN | 101284001 A | 10/2008 |
| CN | 101693730 A | 4/2010 |

OTHER PUBLICATIONS

Devendra, BMJ vol. 328, Mar. 27, 2004.*
Kahn, Annu. Rev. Med. 1996, 47: 509-31.*
Banker, Modern Pharmaceutics, Third Edition, Marcel Dekker, Inc., published 1996, p. 596.*
Sharma et al. International Journal of Pharmacognosy, 1997, vol. 35, No. 2, pp. 130-133.*

* cited by examiner

*Primary Examiner* — Layla Bland
(74) *Attorney, Agent, or Firm* — Shay Glenn LLP

(57) ABSTRACT

Foliamngiferosides having the general formula (I) are disclosed, wherein R is H or —OCH. The preparation method of the compounds, pharmaceutical compositions comprising the compounds as the active ingredients, the use of the compounds and the pharmaceutical compositions for inhibiting the activity of α-glucosidase are also disclosed. The foliamangiferosides can be used in preparing drugs for treating diabetes.

5 Claims, No Drawings

FOLIAMANGIFEROSIDES, PREPARATION METHOD AND USE THEREOF

TECHNICAL FIELD

The present invention relates to the compounds extracted from mango leaves and the preparation method and use thereof, in particular to foliamangiferosides and the preparation method and use thereof.

TECHNICAL BACKGROUND

Mango leaves are the leaves of *Mangifera Indica* L. In traditional Chinese medicine, mango is considered as having sweet and sour taste, mild as a medicine, non-poisonous, which can reach liver channel and spleen channel and is advantageous to stomach. Its action includes generating saliva, quenching thirst, preventing vomiting, promoting urination. It is suitable for treating the conditions such as thirst, dryness of the throat, insufficiency of the stomach property (stomach-qi), vertigo, and vomiting. According to Diet Herbal (Shi Xing Ben Cao), mango can treat the conditions such as channel obstruction (Jing Mai Bu Tong) in females. Supplement to Compendium of Materia Medica (Ben Cao Gang Mu Shi Yi) recorded that mango can prevent sealers from having seasickness after sealers eat mango and that mango can prevent vomiting because it is advantageous to the stomach property. The applications of mango leaves as medicine was first recorded in Lingnan Cai Yao Record (Ling Nan Cai Yao Lu). Luchuan Materia Medica (Lu Chuan Ben Cao), Nanning Medicine Magazine (Nanning Shi Yao Wu Zhi) (First Edition, 1959) and The National Assembly of Chinese Herbal Medicine (Quan Guo Zhong Cao Yao Hui Bian) also stated the applications of mango leaves as medicine under the item of mango. Mango leaves were first stated as a Chinese medicine alone in the Dictionary of Chinese Medicine (Zhong Yao Da Ci Dian) published in 1977. As stated in Standards for Chinese Medicine in Guangxi (Guangxi Zhong Yao Cai Biao Zhun), mango leaves are recorded as tasting sour, sweet, cool and mild, having the function of promoting the circulation of properties (qi), dispersing stagnancy and dispelling measles, which can be used to treat the conditions such as stomachache, property (qi) distension, infantile malnutritional stagnation, thirst and so forth. In China, mango grows in Taiwan, Guangdong, Guangxi, Hainan, Fujian, Yunnan and Sichuan provinces and has a plenty of resources.

The chemical components of mango leaves include ascorbic acid, tannin, mangiferin, ellagic acid, catechol, shikimic acid, quinic acid, kaempferol, thujene and so forth. The prior pharmacology studies indicate that the extracts from mango leaves have functions such as preventing asthma, relieving cough, and eliminating sputum. In 1973, mango leaves were developed into a medicine named Mango Tablets for Relieving Cough by Guangxi College of Chinese Medical and the medicine was approved as one of the National Protected Chinese Medicines in 1998 and was approved as one of the National Essential Medicines in the same year. The typical component in mango leaves is mangiferin, which has the effects such as anti-lipid peroxidation, immunization, Anti-inflammation, Analgesia, liver protection and cholagogue, antivirus, antitumor, central nervous system excitation and so forth.

α-glucosidase exists on the brush border of human intestine and participates the metabolization of saccharides in human body, which play an important role in maintaining the normal physiological functions of human. α-glucosidase cut off glucose from the non-reducing ends of starch and polysaccharide by hydrolyzing α-1,4 glucoside bonds. The absorption of carbohydrates such as starch, dextrin, sucrose, etc. in human body depends on the activity of α-glucosidase. α-glucosidase inhibitor is a medicine used for treating diabetes clinically, which currently obtained from metabolites of microorganism, such as acarbose (tradename: Glucobay), voglibose (tradename: Basen), miglitol, and so forth. Clinical application has proved that acarbose, voglibose and so forth are good medicines for treating diabetes because they have prominent effects of decreasing the Postprandial hyperglycemia for treating type II diabetes. It can be seen that α-glucosidase inhibitors can effectively suppress the activity of α-glucosidase on the brush border of intestine wall so that the degradation of carbohydrates and the adsorption rate of carbohydrates in the alimentary canal are deferred and hindered. Therefore, the glucose absorption derived from disaccharides, oligosaccharides and polysaccharides is deferred, and the time and progress of blood glucose increase in patients are effectively deferred, so α-glucosidase inhibitors are helpful to control the blood glucose increase of type II diabetes.

However, there is still a need for new methods for treating diabetes, for example, type II diabetes. A new research field at present is to look for α-glucosidase inhibitors with high safety from natural products to decrease blood glucose.

DESCRIPTION OF THE INVENTION

In one embodiment, one technical problem solved by the present invention is to provide a novel compound, foliamangiferoside, extracted from mango leaves. In another embodiment, another technical problem solved by the present invention is to provide the preparation method of the foliamangiferoside described above. In still another embodiment, a technical problem solved by the present invention is to provide the use of the foliamangiferoside described above. The present inventors found that a class of novel compounds, i.e. foliamangiferosides can be obtained by separation from mango leaves and the compounds have advantageous biological activity, for example, suitable for preventing and/or treating diabetes such as type II diabetes. The present invention has been accomplished on the basis of the above discovery.

SUMMARY OF THE INVENTION

The first aspect of the present invention provides foliamangiferosides having the following general formula (I):

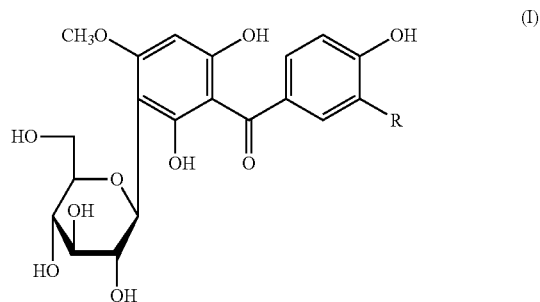

or the isomers, solvates, or prodrugs thereof, wherein,
R is —H or —OCH$_3$.

The second aspect of the present invention provides a method for preparing the foliamangiferosides as described in the first aspect of the present invention, comprising the steps of:

(1) extracting mango leaves with 50% to 95% ethanol or methanol solution, (2) extracting the product in step (1) with a water-immiscible solvent after the alcohol is recovered, discarding the organic solvent layer to remove impurities, (3) enriching the extracted aqueous solution with macroporous adsorptive resins and eluting the product with 50% to 95% ethanol solution, (4) conducting normal phase and reverse phase silica gel chromatography to the eluate from step (3), obtaining the compound foliamangiferosides.

The third aspect of the present invention provides an extract of mango leaves which comprises the foliamangiferosides as described in the first aspect of the present invention.

The fourth aspect of the present invention provides a method for preparing the extract described in the third aspect of the present invention, comprising the steps of:

(1) extracting mango leaves with water or ethanol solution in a certain concentration, (2) transferring the extract solution into aqueous phase after recovering the ethanol, (3) making the aqueous phase to be subject to macroporous adsorptive resins, discarding the effluent and eluting with 50% to 95% ethanol solution, (4) recovering the solvent in the ethanol eluant and distilling to dryness, obtaining the product.

The fifth aspect of the present invention provides a pharmaceutical composition comprising the foliamangiferosides in the first aspect of the present invention or the extract in the third aspect of the present invention in a therapeutically and/or prophylactically effective amount, and optional pharmaceutically acceptable excipients.

The sixth aspect of the present invention provides the use of the foliamangiferosides in the first aspect of the present invention or the extract in the third aspect of the present invention in preparation of medicine for inhibiting the activity of α-glucosidase or as an α-glucosidase inhibitor or for preventing and/or treating diabetes.

The seventh aspect of the present invention provides a method of inhibiting the activity of α-glucosidase or preventing and/or treating diabetes, comprising administrating to the subject in need thereof an effective amount of the foliamangiferosides in the first aspect of the present invention or the extract in the third aspect of the present invention.

The eighth aspect of the present invention provides the foliamangiferosides in the first aspect of the present invention or the extract in the third aspect of the present invention for inhibiting the activity of α-glucosidase or as an α-glucosidase inhibitor or for preventing and/or treating diabetes.

The ninth aspect of the present invention provides a pharmaceutical composition for inhibiting the activity of α-glucosidase or as an α-glucosidase inhibitor or preventing and/or treating diabetes, comprising an effective amount of the foliamangiferosides in the first aspect of the present invention or the extract in the third aspect of the present invention.

DETAILED DESCRIPTION OF THE INVENTION

The present inventor conducted the systematic separation of the plant chemical components of mango leaves, obtaining the compound foliamangiferosides.

Therefore, the first aspect of the present invention provides a foliamangiferoside with the following general formula (I):

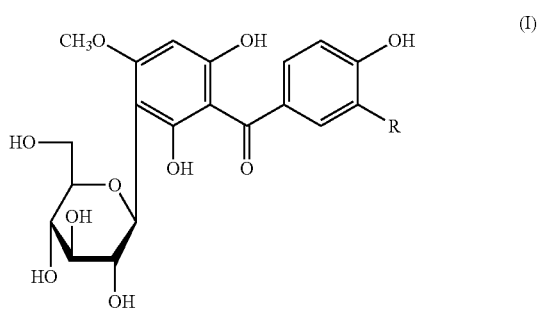

or the isomers, the solvates or the prodrugs thereof, wherein

R is —H or —OCH$_3$.

The foliamangiferoside according to the first aspect of the present invention is foliamangiferoside A when R is —H, which has the following structure formula:

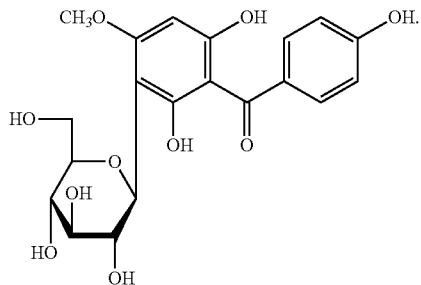

In one embodiment of the first aspect of the present invention, the foliamangiferoside A is pale yellow powders with [α]D25=+21.6° (Concentration: 2.91, methanol). The data obtained by high resolution electrospray mass spectrometry are as following: calculated for $C_{20}H_{21}O_{10}$ (M–H)$^-$ 421.1140, found 421.1149. Infrared spectrum data (KBr, cm$^{-1}$) are: 3281, 2924, 2855, 1653, 1622, 1558, 1459, 1085, 1017. $^1$H NMR (400 MHz, dimethyl sulfoxide (_DMSO)): 3.21 (2H, m, overlap, 1"-H and 5"-H), 3.22 (1H, m, 3"-H), 3.49 (1H, m, overlap, 2"-H), [3.49 (1H, m, overlap), 3.59 (1H, broad d, J=11 Hz), 6"-H2], 3.69 (3H, s, 4-OCH3), 4.62 (1H, d, J=9.6 Hz, 1"-H), 6.06 (1H, s, 5-H), 6.79 (2H, d, J=8.4 Hz, 3',5'-H), 7.59 (2H, d, J=8.4 Hz, 2',6'-H). $^{13}$C NMR (100 MHz, DMSO) 109.0 (C-1), 155.7 (C-2), 104.6 (C-3), 159.5 (C-4), 91.4 (C-5), 156.4 (C-6), 130.2 (C-1'), 131.7 (C-2'), 114.9 (C-3'), 161.9 (C-4'), 114.9 (C-5'), 131.7 (C-6'), 74.7 (C-1"), 71.9 (C-2"), 78.2 (C-3"), 69.5 (C-4"), 81.1 (C-5"), 60.3 (C-6"), 193.8 (C=O), 55.6 (OCH3-3').

The foliamangiferoside according to the first aspect of the present invention is foliamangiferoside B when R is —OCH$_3$, which has the following structure formula:

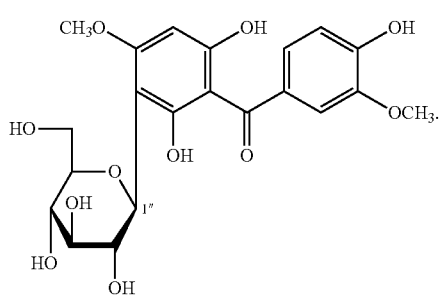

In one embodiment of the first aspect of the present invention, the foliamangiferoside B is pale yellow powders with

[α]D25 =+2.5° (Concentration: 0.67, methanol). The data of high resolution electrospray mass spectrometry are: calculated for $C_{21}H_{23}O_{11}$ (M−H)⁻ 451.1246; found 451.1246. Infrared spectrum (KBr, cm⁻¹): 3281, 2922, 2852, 1650, 1626, 1560, 1464, 1081. ¹H NMR (400 MHz, DMSO): 3.21 (3H, m, overlap, 3", 4" and 5"-H), [3.53 (1H, m, overlap), 3.60 (1H, broad d, ca. J=11 Hz), 6"-H2], 3.55 (1H, m, overlap, 2"-H), 3.70 (3H, s, 4-OCH3), 3.79 (3H, s, 3'-OCH3), 4.63 (1H, d, J=9.6 Hz, 1"-H), 6.79 (1H, d, J=8.0 Hz, 5'-H), 7.16 (1H, bd, ca. J=8 Hz, 6'-H), 7.35 (1H, bs, 2'-H). ¹³C NMR (100 MHz, DMSO) 108.9 (C-1), 155.6 (C-2), 104.4 (C-3), 159.3 (C-4), 91.3 (C-5), 156.4 (C-6), 130.2 (C-1'), 111.5 (C-2'), 147.3 (C-3'), 151.6 (C-4'), 114.6 (C-5'), 124.9 (C-6'), 74.6 (C-1"), 71.8 (C-2"), 78.0 (C-3"), 69.3 (C-4"), 80.9 (C-5"), 60.2 (C-6"), 193.6 (C=O), 55.5 (OCH3-3', OCH3-4).

The second aspect of the present invention provides the preparation method of the foliamangiferoside according to the first aspect of the present invention, comprising the steps of:
(1) extracting mango leaves with 50% to 95% ethanol or methanol solution,
(2) extracting with a water-immiscible solvent the product in step (1) after the alcohol is recovered, discarding the organic solvent layer to remove impurities,
(3) enriching the extracted aqueous solution with macroporous adsorptive resins and eluting the product with 50% to 95% ethanol solution,
(4) conducting normal phase and reversed phase silica gel chromatography to the eluate from step (3), obtaining the compound foliamangiferoside.

In one embodiment of the preparation method according to the second aspect of the present invention, said water-immiscible organic solvent is selected from ethyl acetate.

In one embodiment of the preparation method according to the second aspect of the present invention, said step (2) can be omitted, i.e. the extract obtained in step (1) can be concentrated and then hydrolyzed, then subject to step (3) to conduct the adsorption in macroporous adsorptive resins. Although the yield might be decreased without step (2), the object of the present invention can still be achieved.

The third aspect of the present invention provides an extract of mango leaves, comprising the foliamangiferoside according to the first aspect of the present invention.

The amount of the foliamangiferosides in the extract according to the third aspect of the present invention is greater than 1% (w/w), greater than 2% (w/w), greater than 3% (w/w), greater than 4% (w/w), or greater than 5% (w/w) of the total amount of the extract. It should be appreciated that the "amount of foliamangiferosides" refers to the total amount of the various foliamangiferosides if said extract contains more than one kind of foliamangiferoside according to the first aspect of the present invention.

The extract according to the third aspect of the present invention contains foliamangiferoside A and the amount of said foliamangiferoside A is greater than 1% (w/w), greater than 2% (w/w), greater than 3% (w/w), or greater than 4% (w/w) of the total amount of the extract.

The extract according to the third aspect of the present invention contains foliamangiferoside B and the amount of said foliamangiferoside B is greater than 0.005% (w/w), greater than 0.01% (w/w), or greater than 0.015% (w/w) of the total amount of the extract.

The extract according to the third aspect of the present invention contains foliamangiferoside A and B and the weight ratio of foliamangiferoside A to foliamangiferoside B is 50 to 500:1, or 100 to 400:1, or 150 to 350:1, or 200 to 300:1.

The extract according to the third aspect of the present invention can be obtained by the preparation method comprising the following steps of:
(1) extracting mango leaves with water or ethanol solution in a certain concentration,
(2) transferring the extracting solution into aqueous phase after recovering the ethanol,
(3) conducting adsorption to the aqueous phase with macroporous adsorptive resins, discarding the effluent and eluting with 50% to 95% ethanol solution,
(4) recovering the ethanol in the alcoholic eluant and distilling to dryness, obtaining the product.

The extract according to the third aspect of the present invention can be obtained by the preparation method comprising the following steps of:
(1) extracting mango leaves with 50% to 95% ethanol or methanol solution,
(2) extracting the resultant solution with a water-immiscible organic solvent after recovering the alcohol in the solution, then discarding the organic solvent layer to remove the impurities,
(3) enriching the extracted aqueous solution with macroporous adsorptive resins, eluting with 50%-95% ethanol solution, obtaining the extract, and optionally,
(4) conducting normal phase silica gel chromatography of the extract obtained in step (3), obtaining the extract.

In an embodiment, the water-immiscible organic solvent of step (2) as above is selected from ethyl acetate. In one embodiment, the step (3) comprises the step of pre-eluting with a low concentration of ethanol solution (for example, 10% to 25% ethanol) before conducting the elution with ethanol.

The fourth aspect of the present invention provides the method of preparing the extract according to the third aspect of the present invention, comprising the steps of:
(1) extracting mango leaves with water or ethanol solution in certain concentration,
(2) transferring the extracting solution into aqueous phase after recovering the ethanol,
(3) conducting absorption to the aqueous solution phase with macroporous adsorptive resins, discarding the effluent and eluting with 50% to 95% ethanol solution,
(4) recovering the ethanol in the alcoholic eluant and distilling to dryness, obtaining the product.

The fourth aspect of the present invention also provides a method of preparing the extract according to the third aspect of the present invention, comprising the steps of:
(1) extracting mango leaves with an 50% to 95% ethanol or methanol solution,
(2) extracting the resultant solution with a water-immiscible organic solvent after recovering the alcohol in the solution, then discarding the organic solvent layer to remove the impurities,
(3) enriching the extracted aqueous solution with macroporous adsorptive resins, eluting with 50%-95% ethanol solution, obtaining the extract, and optionally,
(4) further conducting normal phase silica gel chromatography to the extract obtained in step (3), obtaining the extract.

The method according to the fourth aspect of the present invention further comprises a step of pre-eluting with a low concentration of aqueous ethanol solution (for example 10 to 25% ethanol) before eluting with ethanol in the step (3).

The method according to the fourth aspect of the present invention comprises the steps of:
(1) extracting mango leaves with water or ethanol solution in certain concentration, (2) transferring the extracting solution into water phase after recovering the ethanol, (3) absorbing with macroporous adsorptive resins and discarding the effluent, then pre-eluting with a low concentration of 10 to 25% ethanol solution and discarding the effluent before eluting with 50% to 95% aqueous ethanol solution, (4) recovering the alcoholic eluant and distilling to dryness, obtaining the product.

The fifth aspect of the present invention provides a pharmaceutical composition, comprising a therapeutically and/or prophylactically effective amount of the foliamangiferosides according to the first aspect of the present invention or the extract according to the third aspect of the present invention, and optional pharmaceutically acceptable excipients.

The sixth aspect of the present invention provides use of the foliamangiferosides according to the first aspect of the present invention or the extract according to the third aspect of the present invention in preparation of medicine for inhibiting the activity of α-glucosidase.

The sixth aspect of the present invention further provides the use of the foliamangiferosides according to the first aspect of the present invention or the extract according to the third aspect of the present invention in preparation of medicine as α-glucosidase inhibitors.

The sixth aspect of the present invention further provides the use of the foliamangiferosides according to the first aspect of the present invention or the extract according to the third aspect of the present invention in preparation of medicine for treating and/or preventing diabetes. In one embodiment, said diabetes is type II diabetes.

The seventh aspect of the present invention provides a method of inhibiting the activity of α-glucosidase, which comprises administering an effective amount of the foliamangiferosides according to the first aspect of the present invention or the extract according to the third aspect of the present invention to the subject in need thereof.

The seventh aspect of the present invention further provides a method of preventing and/or treating diabetes, which comprises administering an effective amount of foliamangiferosides according to the first aspect of the present invention or the extract according to the third aspect of the present invention to the subject in need thereof. In one embodiment, said diabetes is type II diabetes.

The eighth aspect of the present invention provides the foliamangiferosides according to the first aspect of the present invention or the extract according to the third aspect of the present invention used for inhibiting the activity of α-glucosidase.

The eighth aspect of the present invention further provides the foliamangiferosides according to the first aspect of the present invention or the extract according to the third aspect of the present invention as α-glucosidase inhibitors.

The eighth aspect of the present invention further provides the foliamangiferosides according to the first aspect of the present invention or the extract according to the third aspect of the present invention used for preventing and/or treating diabetes. In one embodiment, said diabetes is type II diabetes.

The ninth aspect of the present invention provides a pharmaceutical composition for inhibiting the activity of α-glucosidase, which comprises an effective amount of the foliamangiferosides according to the first aspect of the present invention or the extract according to the third aspect of the present invention.

The ninth aspect of the present invention further provides a pharmaceutical composition as an α-glucosidase inhibitor, which comprises an effective amount of the foliamangiferosides according to the first aspect of the present invention or the extract according to the third aspect of the present invention.

The ninth aspect of the present invention further provides a pharmaceutical composition for preventing and/or treating diabetes, which comprises an effective amount of the foliamangiferosides according to the first aspect of the present invention or the extract according to the third aspect of the present invention. In one embodiment, said diabetes is type II diabetes.

The feature or features in any one aspect of the present invention or any one sub-aspect of any one aspect of the present invention can be used in any other aspect of the present invention or any sub-aspect of any one aspect of the present invention, or the feature or features in any one sub-aspect of any one aspect of the present invention can be used in any other sub-aspect of the aspect of the present invention as long as there are no conflict between the features. The features can be modified suitably if necessary when there is a conflict between the features.

The various aspects and features of the present invention will be further described as follows.

The references referred to in the present invention are incorporated herein by reference. The meaning stated in the references will have the meaning as stated in the present invention where the meaning stated in the reference is different with that in the present invention. Besides, the terms and phrases used in the present invention have the common meaning as known by the persons skilled in the art. Even so, a detailed explanation of these terms and phrases will be given in the present invention. The mentioned terms and phrases will have the meaning as stated in the present invention if they have different meaning with the known meaning in the art.

The term "about" as used herein usually refers to the acceptable range of error in the art, for example, ±10%, or ±5%, or ±2%.

As described herein, the term "effective amount" refers to the amount which is used to treat, to prevent, to abate and/or to alleviate the mentioned diseases or conditions.

As stated herein, the term "pharmaceutical composition", exchangeable with "composition", refers to combination of matters, which can treat, prevent, abate and/or alleviate the mentioned diseases or conditions.

As stated herein, the term "subject", or "patient", refers to animals that can accept the foliamangiferosides of the present invention or the extract of the present invention, in particular mammals such as human, dog, monkey, cow or horse, etc., to treat, prevent, abate and/or alleviate the diseases or conditions mentioned in the present invention.

As stated herein, the term "disease or condition" refers to a body condition of the subject which is related to the diseases or conditions described in the present invention.

As stated herein, the term "%", unless explicitly expressed otherwise, refers to percentages of weight/weight for solid matters, refers to percentages of weight/volume for liquid matters, or refers to percentages of volume/volume where both the solute and the solvent are liquid. The expression "%" when refers to ethanol, for example 95% ethanol, has the meaning well known in the art (for example, see the definition in the General Notices in <Volume II PHARMACOPOEIA OF THE PEOPLES REPUBLIC OF CHINA>, Edition 2005).

As stated herein, the term "extract", unless explicitly expressed otherwise, refers to the "extract" obtained from mango leaves after extraction.

As stated herein, the term "(w/w)", unless explicitly expressed otherwise, refers to weight/weight ratio. Similarly, (w/v) refers to weight/volume ratio.

As stated herein, the term "mango leaves", unless explicitly expressed otherwise, refers to dried mango leaves.

The "pharmaceutically acceptable excipient" can be any typical excipient in pharmaceutical formulations. The selection of specific excipient depends on the delivering routes or the types or conditions of disease of the specific patient. The preparation methods of the pharmaceutical compositions suitable for specific delivering routes are well known to a person skilled in the art. For example, the pharmaceutically acceptable excipients include diluents, carriers, fillers, binders, wetting agents, disintegrants, absorption enhancers, surfactants, adsorption carriers and lubricants, and so forth which are well known in the pharmaceutical field. If necessary, flavouring agents, preservatives and sweeting agents can be added in the pharmaceutical composition.

The pharmaceutical composition of the present invention can be prepared in the form of tablet, powder, particle, capsule, oral liquid, ointment, cream, emulsion for injection (sterile powder for injection) and so forth. The medicine in the form described above can be prepared in the typical methods in the pharmaceutical field.

The $\alpha$-glucosidase described in the present invention exists on the intestinal brush border of human body and participates in the metabolism of saccharides in human body, which plays an important role in maintaining the normal physiological function of human bodies. $\alpha$-glucosidase cut off glucose from the non-reducing end of starch and polysaccharides by hydrolyzing the $\alpha$-1,4glycoside bond. The absorption of carbohydrates such as starch, dextrin, sugar and so forth in human bodies depends on the activity of the enzyme on the intestinal brush border. $\alpha$-glucosidase inhibitor is a kind of medicine for treating diabetes clinically and has a remarkable effect of reducing postprandial hyperglycemia when used to treat type II diabetes, so it is a good medicine for treating diabetes. $\alpha$-glucosidase inhibitor suppresses the activity of $\alpha$-glucosidase on the intestinal brush border in a reversible competition way and thus defers and impedes the degradation of carbohydrates and the absorption rate of carbohydrates in alimentary canal, defers the absorption of glucose derived from disaccharides, oligosaccharides and polysaccharides, effectively defers and alleviates the time and progress of postprandial hyperglycemia of patients with diabetes, and helps to control the blood sugar rises of type II diabetes.

$\alpha$-glucosidase inhibitor is mainly suitable for treating the patients with the type II diabetes with postprandial hyperglycemia, in particular obesity person and aged people, and can combine with other oral hypoglycemic drugs or insulin for the patients with fasting hyperglycemia and postprandial hyperglycemia. $\alpha$-glucosidase inhibitor can reduce the risk of patients with impaired glucose tolerance to change into diabetes, so it can be used in intervention treatment of patients with impaired glucose tolerance. The effect of hypoglycemic drugs such as sulfonylureas and biguanides are not satisfied to patients with type II diabetes, particularly when they are used to control postprandial blood glucose, so $\alpha$-glucosidase inhibitor can be combined with hypoglycemic drugs. This combination can be used for the patients whose blood sugar cannot be controlled satisfactorily only through diet therapy, especially used for obesity person. For patients with Type I diabetes, $\alpha$-glucosidase inhibitor can be uses as an adjunctive therapeutic drug.

$\alpha$-glucosidase inhibitor is hardly absorbed by intestinal tract into blood, so it has little effect on liver and kidney and thus has little system side effect. $\alpha$-glucosidase inhibitor only defers rather than completely blocks the metabolism and absorption of carbohydrates. The total amount of the absorption of the carbohydrates in human bodies will not be decreased. Therefore, the heat amount will not be lost. $\alpha$-glucosidase inhibitor will not inhibit the absorption of proteins and fats, so it will not lead to malabsorption of nutrients.

The compounds, foliamangiferosides, are obtained by separating from mango leaves according to the present invention. In particular, foliamangiferoside A and foliamangiferoside B are the novel compounds which are found for the first time. The study on the activity of $\alpha$-glucosidase inhibition in vitro indicates that foliamangiferosides have very strong effect of inhibiting the activity of $\alpha$-glucosidase and the extract of mango leaves containing the foliamangiferosides also have strong effect of inhibiting the activity of $\alpha$-glucosidase. Therefore, foliamangiferosides can be expected to be used for the preparation of medicines for treating diabetes so that the object of treating diabetes can be achieved.

New compound, foliamangiferosides, are found by conducting the separation from mango leaves. The compounds are found for the first time. The experiment on the activity of $\alpha$-glucosidase inhibition indicates that the foliamangiferosides have very strong effect of inhibiting the $\alpha$-glucosidase activity, thus it can be expected to be used for preparation of drugs for treating diabetes so that the object of treating diabetes can be achieved.

Embodiments

The technical solutions of the present invention will be described in more detail in the following to make the persons skilled in the art understand the technical solutions of the present invention more clearly. In the following examples, unless stated otherwise, said mango leaves refer to the dried mango leaves with batch No. 090722, purchased from HEBEI ANGUO QIXIN TRADITIONAL CHINESE MEDICINE GRANULA CO., LTD.

Example 1

Preparation of Active Ingredient
Foliamangiferoside A

Step 1: Mango leaves (batch No. 90722, dried, 5 kg) are refluxed and extracted twice with ethanol in the amount of 9 times that of the mango leaves, 3 hours each time. The filtrates are combined, then dried in vacuum drier (50° C.) after the solvent is recovered. The extract (or concrete) (1.163 kg) is obtained.

Step 2: 600 g of the extract as above is dissolved in 5 L of distilled water, then extracted with ethyl acetate (5L) three times. An ethyl acetate layer and an aqueous layer are obtained, respectively. The aqueous layer contains a large amount of precipitates. 4/5 of the aqueous suspension layer is concentrated under reduced pressure to 2 L, then centrifuged and filtered. The supernatant is treated with macroporous adsorptive resins ($H_2O \rightarrow 95\%$ EtOH) and a 95% ethanolic eluate (84 g) is obtained.

Step 3: 72 g of the 95% ethanolic eluate as above is subjected to silica gel column chromatography (chloroform-methanol (10:1→5:1)→chloroform-methanol-water (7:3:1→6:4:1, lower layer)→methanol) and 9 fractions are obtained, wherein fraction No. 6 is 9.0 g).

Step 4: 7.0 g of the fraction No. 6 obtained in step 3 is subjected to reverse phase ODS column chromatography (methanol-water (10%→20%→30%→40%→50%→100%), and 7 fractions (designated as fraction 6-1, fraction 6-2, fraction 6-3, fraction 6-4, fraction 6-5, fraction 6-6, and fraction 6-7) are obtained, wherein fraction 6-2, 6-3 and 6-4 are 4.9 g, 0.2 g and 0.6 g, respectively.

Step 5: The resultant fraction 6-2 in step 4 is prepared by preparative high performance liquid chromatography (chromatography conditions: pump: k-501, detector: Waters 2487, temperature: room temperature, column: Cosmosil packed column 5C18-MS-II (Size 20 I.D.×250 mm), mobile phase: MeOH:H$_2$O (20:80)+1% HAc, flow rate: 9.0 ml/min), and a single compound (4.2 g) is obtained, which is identified as a new compound foliamangiferoside A.

The physicochemical properties of the foliamangiferoside A: pale yellow powder, [α]D25+21.6° (concentration: 2.91, methanol). The data of electrospray ionization high resolution mass spectrum: calculated for $C_{20}H_{21}O_{10}$ (M–H) 421.1140, found 421.1149. Infrared spectrum (KBr, cm$^{-1}$): 3281, 2924, 2855, 1653, 1622, 1558, 1459, 1085, 1017. $^1$H NMR (400 MHz, DMSO): 3.21 (2H, m, overlap, 1"-H and 5"-H), 3.22 (1H, m, 3"-H), 3.49 (1H, m, overlap, 2"-H), [3.49 (1H, m, overlap), 3.59 (1H, broad d, J=11 Hz), 6"-H2], 3.69 (3H, s, 4-OCH3), 4.62 (1H, d, J=9.6 Hz, 1"-H), 6.06 (1H, s, 5-H), 6.79 (2H, d, J=8.4 Hz, 3',5'-H), 7.59 (2H, d, J=8.4 Hz, 2',6'-H). $^{13}$C NMR(100 MHz, DMSO) 109.0 (C-1), 155.7 (C-2), 104.6 (C-3), 159.5 (C-4), 91.4 (C-5), 156.4 (C-6), 130.2 (C-1'), 131.7 (C-2'), 114.9 (C-3'), 161.9 (C-4'), 114.9 (C-5'), 131.7 (C-6'), 74.7 (C-1"), 71.9 (C-2"), 78.2 (C-3"), 69.5 (C-4"), 81.1 (C-5"), 60.3 (C-6"), 193.8 (C=O), 55.6 (OCH3-3').

The structure formula of the foliamangiferoside A is determined as following based on its physicochemical properties:

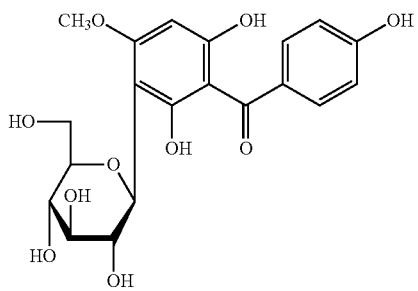

The compound has not reported in the prior art, which is obtained by separation for the first time.

Example 2

Preparation of Active Ingredient Foliamangiferoside B

The fraction 6-4 obtained in step 4 of example 1 is subjected to preparative high performance liquid chromatography (chromatography conditions: pump: k-501, detector: Waters 2487, temperature: room temperature, column: Cosmosil packed column 5C18-MS-II (Size 20 I.D.×250 mm), mobile phase: MeOH:H$_2$O (30:70)+1% HAc and MeOH:H$_2$O (20:80), flow rate: 9.0 ml/min), and a single compound (0.06 g) is obtained, which is identified as a new compound according to its physicochemical properties and nuclear magnetic resonance, and named as foliamangiferoside B.

The physicochemical properties of foliamangiferoside B: pale yellow powders, [α]D25=+2.5° (concentration: 0.67, methanol). The data of electrospray ionization high resolution mass spectrum: calculated for $C_{21}H_{23}O_{11}$ (M–H) 451.1246; found 451.1246. Infrared spectrum (KBr, cm$^{-1}$): 3281, 2922, 2852, 1650, 1626, 1560, 1464, 1081. $^1$H NMR (400 MHz, DMSO): 3.21 (3H, m, overlap, 3", 4" and 5"-H), [3.53 (1H, m, overlap), 3.60 (1H, wide d, ca. J=11 Hz), 6"-H2], 3.55 (1H, m, overlap, 2"-H), 3.70 (3H, s, 4-OCH3), 3.79 (3H, s, 3'-OCH3), 4.63 (1H, d, J=9.6 Hz, 1"-H), 6.79 (1H, d, J=8.0 Hz, 5'-H), 7.16 (1H, wide d, ca. J=8 Hz, 6'-H), 7.35 (1H, wide s, 2'-H). $^{13}$C NMR (100 MHz, DMSO) 108.9 (C-1), 155.6 (C-2), 104.4 (C-3), 159.3 (C-4), 91.3 (C-5), 156.4 (C-6), 130.2 (C-1'), 111.5 (C-2'), 147.3 (C-3'), 151.6 (C-4'), 114.6 (C-5'), 124.9 (C-6'), 74.6 (C-1"), 71.8 (C-2"), 78.0 (C-3"), 69.3 (C-4"), 80.9 (C-5"), 60.2 (C-6"), 193.6 (C=O). 55.5 (OCH3-3', OCH3-4).

The structure of the foliamangiferoside B is determined as following based on the physicochemical properties:

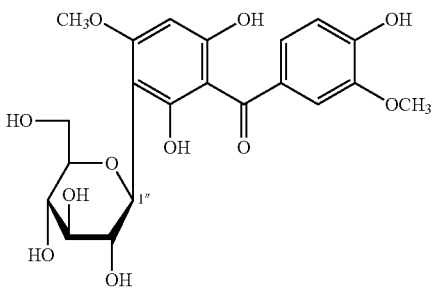

The compound foliamangiferoside B is not reported in the prior art, which is obtained by separation for the first time.

Example 3

Experimental Study on the Hypoglycemic Effect of the Compounds of the Present Invention The research process of α-glucosidase inhibiting activity: A Wistar male rat (body weight: about 200 g) is sacrificed by decapitation. The jejunum is taken out. The brush border membrane is scraped and then mixed into 0.1 M maleic acid buffer solution (pH 6.0). The mixture is used as α-glucosidase crude enzyme. 50 uL of sample solution dissolved in 2.5% DMSO is added into 100 uL of 74 mN sucrosebase solution, into which 50 uL of the α-glucosidase solution derived from rat intestines is added. The mixture is reacted for 30 minutes at 37° C. before adding 800 uL of water and placing into boiling water bath for 2 minutes to be inactivated. The amount of the glucose produced is assayed with glucose assay kits.

Preparation of Sample Solution Group 0.1 M of maleic acid aqueous solution is mixed with 0.1 M of sodium maleate aqueous solution. The mixture is adjusted to pH 6.0 and is used as 0.1 M of maleic acid buffer solution. A sample is dissolved into DMSO solution and diluted 10 times with 0.1 M of maleic acid buffer solution. A sample solution is obtained and ready to use.

Sample group: The group in which a sample is added according to the experimental procedure described above (the samples are foliamangiferoside A (obtained in example 1) and foliamangiferoside B (obtained in example 2)); Control group: The group in which 2.5% DMSO solution is added according to the experimental procedure described above; Blank group: The type and amount of the agents are the same with those in sample group except that 800 uL of water is added immediately after 50 uL of the α-glucosidase solution derived from rat intestines is added, then the mixture is placed into a boiling water bath for 2 minutes to conduct inactivation.

Furthermore, the similar experiments are conducted with ethanolic extracts of mango leaves (the product obtained in step 1 of example 1).

The following equation is used to calculate the inhibition ratio (%):

inhibition ratio (%)=$(A-B)/(A-C)*100$ wherein, A is the absorbance of control group, B is the absorbance of sample group and C is the absorbance of blank group.

The results for single compound can be seen in Table 1 and the results for extract can be seen in Table 2.

The results in Table 1 indicates that, with the concentration of 400 uM, the inhibition ratios of foliamangiferoside A and foliamangiferoside B are 58.2% and 45.6%, respectively, which indicates that foliamangiferoside A and B can effectively inhibit the conversion of sucrose into glucose under the catalysis of α-glucosidase in intestines. It can be seen from the results in Table 2 that the extract according to the present invention can also inhibit the conversion of sucrose into glucose under the catalysis of α-glucosidase in intestines.

Preparation of controls: 1.8 mg of the foliamangiferoside A obtained in Example 1, 2.3 mg of the foliamangiferoside B obtained in Example 2 are placed in a 10 ml volumetric flask and are dissolved by adding methanol to the scale.

Preparation of samples: 500 mg of mango leaves with batch no. 090722 is placed into 25 ml conical flask with cover into which 50 ml of methanol is added. The extraction is conducted for 30 minutes under ultrasonic wave before weighting. Methanol is used to supplement the weight and the sample solution is obtained. The sample solution is subject to HPLC after centrifuged in high speed of 14000 rpm.

The Results of Assay:

Control solution and sample solution are sampled 10 μL, respectively. The contents of foliamangiferoside A and foliamangiferoside B in mango leaves are calculated as 0.20% (w/w) and 0.0013% (w/w), respectively.

TABLE 1

The inhibition ratios of foliamangiferoside A and foliamangiferoside B on the α-glucosidase in intestines

| | Foliamangiferoside A | | | Foliamangiferoside B | | |
| --- | --- | --- | --- | --- | --- | --- |
| Conc. (uM) | Blank group Conc. of glucose hydrolyzed (mg/dl) | Sample group Conc. of glucose hydrolyzed (mg/dl) | Inhibition ratio | Blank group Conc. of glucose hydrolyzed (mg/dl) | Sample group Conc. of glucose hydrolyzed (mg/dl) | Inhibition ratio |
| 0 | 1.08 | 6.10 | 0.0% | 0.95 | 6.21 | 0.0% |
| 50 | 1.00 | 5.23 | 15.8% | 1.00 | 5.23 | 19.6% |
| 100 | 0.64 | 4.64 | 20.2% | 0.64 | 4.64 | 23.9% |
| 200 | 0.42 | 4.12 | 26.2% | 0.42 | 4.12 | 29.6% |
| 400 | 0.99 | 3.09 | 58.2% | 0.85 | 3.71 | 45.6% |

TABLE 2

The inhibition ratios of ethanolic extract of mango leaves on the α-glucosidase in intestines

| Conc. (ug/ml) | Blank group Conc. of glucose hydrolyzed (mg/dl) | Sample group Conc. of glucose hydrolyzed (mg/dl) | Inhibition ratio |
| --- | --- | --- | --- |
| 0 | 0.83 | 5.88 | 0.0% |
| 50 | 1.05 | 5.06 | 20.6% |
| 100 | 0.79 | 4.88 | 19.0% |
| 200 | 0.86 | 4.74 | 23.2% |
| 400 | 0.91 | 3.50 | 48.7% |

Example 4

Determination of the Contents of Foliamangiferoside A and Foliamangiferoside B in Mango Leaves Instruments and Chromatographic Method:
High Performance Liquid Chromatography: Waters 600 system
Detector: Water 2487 ultraviolet detector
Column: Cosmosil packed column 5C18-MS-II (5 μm, 4.6×250 mm)
Mobile phase: methanol-1% acetic acid aqueous solution (3:7)
Detecting wavelength: 254 nm
Flow rate: 0.8 ml/min Example 5

Preparation of Extract Containing Foliamangiferoside A and Foliamangiferoside B

Mango leaves (5 kg) are refluxed and extracted twice with 80% ethanol of 9 times the amount of the mango leaves, 3 hours each time. The filtrates are combined, and then water is added to a total volume of 10000 ml after the solvent is recovered. The solution is refrigerated overnight. The supernatant is subject to the treatment with pre-treated macroporous adsorptive resins and the effluent is discarded, then washed with 2 BV of water (BV=column volume) and eluted with 95% ethanol. The ethanolic eluant is vacuum dried after the ethanol is recovered and the extract of mango leaves (180 g) is obtained. The batch number is 090822.

Following the method in example 4, the conents of foliamangiferoside A and foliamangiferoside B are determined as 5.2% (w/w) and 0.022% (w/w) respectively in the extract obtained in the example. The weight ratio of foliamangiferoside A to foliamangiferoside B in the extract is 236:1.

Example 6

Preparation of Extract Containing Foliamangiferoside A and Foliamangiferoside B

Mango leaves (5 kg) are refluxed and extracted twice with 80% ethanol of 9 times the amount of the mango leaves, 3 hours each time. The filtrates are combined, and then water is added to a total volume of 10000 ml after the solvent is recovered. The solution is refrigerated overnight. The supernatant is subject to the treatment with pre-treated macroporous adsorptive resins and the effluent is discarded, then washed with 2 BV of water (BV=column volume) and pre-eluted with 2 BV of 20% ethanol solution while discarding the eluate before eluted with 80% ethanol. The ethanolic eluant is vacuum dried after the ethanol is recovered and the extract of mango leaves (220 g) is obtained. The batch number is 090902.

Following the method in example 4, the contents of foliamangiferoside A and foliamangiferoside B are determined as 4.7% (w/w) and 0.019% (w/w) respectively in the extract obtained in the example. The weight ratio of foliamangiferoside A to foliamangiferoside B in the extract is 247:1.

Example 7

Preparation of Mango Hypoglycemic Oral Solution 2 g of the extract of mango leaves (obtained from Example 6) is added into and dissolved in 400 ml of distilled water. The solution is filtered, into which an appropriate amount of simple syrup, sodium benzoate are added. 1000 ml of the total volume is reached by adding distilled water. The resultant solution is refrigerated and filtered, sealed in 10 ml of ampoules and sterilized for 30 minutes at 100° C. The product is obtained.

Example 8

Preparation of Mango Hypoglycemic Tablets 4 g of the extract of mango leaves (obtained from Example 6) is comminuted, into which 100 g of starch, 50 g of lactose, an appropriate amount of ethyl cellulose and crospovidone are added. The mixture is granulated with 50%-95% ethanol, dried and finished, then added into the remaining amount of crospovidone and magnesium stearate, pressed into tablets. The product is obtained.

Example 9

Preparation of Mango Hypoglycemic Capsules 4 g of the extract of mango leaves (obtained from Example 6) is comminuted, into which an appropriate amount of magnesium stearate is added. The product is obtained by filling the mixture into capsules.

Example 10

Preparation of Mango Hypoglycemic Tablets

Into 0.5 g of foliamangiferoside A (obtained from Example 6), 100 g of starch, 50 g of lactose, an appropriate amount of ethyl cellulose and crospovidone are added. The mixture is granulated with 50%-95% ethanol, dried and finished, then added into the remaining amount of crospovidone and magnesium stearate, pressed into tablets. The product is obtained.

Example 11

Preparation of Mango Hypoglycemic Capsules

Into 0.5 g of foliamangiferoside B (obtained from Example 6), 100 g of galactose and an appropriate amount of magnesium stearate are added. The product is obtained by filling the mixture into No. 2 capsules.

The foliamangiferosides, extract, and the preparation method and use thereof according to the present invention are described above with reference to the specific examples. It will be appreciated that these examples are illustrative rather than limiting. A person skilled in the art may give a plenty of examples within the scope of the present invention as stated in the appended claims. All these change and modification within the spirit of the present invention shall be included in the scope of the present invention.

The invention claimed is:

1. An isolated foliamangiferoside as expressed in general formula (I)

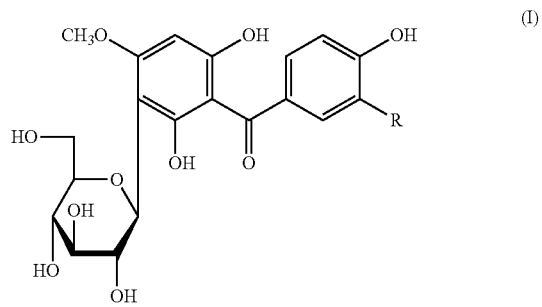

or isomers or solvates thereof, wherein R is —H or —OCH$_3$.

2. The foliamangifero side according to claim 1, which is

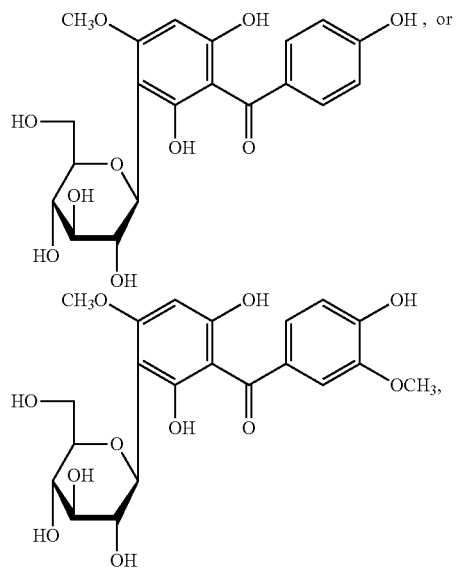

or isomers or solvates thereof.

3. A pharmaceutical composition comprising a therapeutically effective amount of the foliamangiferoside according to claim 1 for treating diabetes and optional pharmaceutically acceptable excipients.

4. A method for treating diabetes, comprising administering an effective amount of the foliamangifero side according to claim 1 to a subject in need thereof.

5. The foliamangiferoside according to claim 1, which is
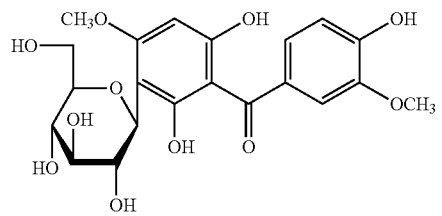
or isomers or solvates thereof.
\* \* \* \* \*

UNITED STATES PATENT AND TRADEMARK OFFICE
CERTIFICATE OF CORRECTION

PATENT NO. : 8,829,167 B2  
APPLICATION NO. : 13/501208  
DATED : September 9, 2014  
INVENTOR(S) : Tao Wang et al.

Page 1 of 1

It is certified that error appears in the above-identified patent and that said Letters Patent is hereby corrected as shown below:

In the Claims

Column 16, line 33; after "2. The" and before "according to claim 1", delete "foliamangifero side" and insert --foliamangiferoside--.

Column 16, line 66; after "amount of the" and before "according", delete "foliamangifero side" and insert --foliamangiferoside--.

Signed and Sealed this  
Tenth Day of February, 2015

Michelle K. Lee  
*Deputy Director of the United States Patent and Trademark Office*